(12) United States Patent
Froster et al.

(10) Patent No.: US 10,646,345 B2
(45) Date of Patent: May 12, 2020

(54) IMPLANT WITH HOLE HAVING POROUS STRUCTURE FOR SOFT TISSUE FIXATION

(71) Applicant: Howmedica Osteonics Corp., Mahwah, NJ (US)

(72) Inventors: Kevin Froster, Marlboro, NJ (US); Mark Gruczynski, Kinnelon, NJ (US); Amber Fox, Wharton, NJ (US); Joseph Peter Nessler, Saint Cloud, MN (US)

(73) Assignee: Howmedica Osteonics Corp., Mahwah, NJ (US)

( * ) Notice: Subject to any disclaimer, the term of this patent is extended or adjusted under 35 U.S.C. 154(b) by 23 days.

(21) Appl. No.: 15/995,394

(22) Filed: Jun. 1, 2018

(65) Prior Publication Data

US 2018/0344463 A1    Dec. 6, 2018

Related U.S. Application Data

(60) Provisional application No. 62/514,318, filed on Jun. 2, 2017.

(51) Int. Cl.
*A61B 17/04* (2006.01)
*A61F 2/28* (2006.01)
(Continued)

(52) U.S. Cl.
CPC ........ *A61F 2/2846* (2013.01); *A61B 17/0401* (2013.01); *A61B 17/06166* (2013.01); *A61B 17/68* (2013.01); *A61B 17/866* (2013.01); *A61F 2/367* (2013.01); *A61F 2/389* (2013.01); *A61F 2/4059* (2013.01); *A61B 17/842* (2013.01); *A61B 2017/00955* (2013.01); *A61B 2017/042* (2013.01); *A61B 2017/0414* (2013.01); *A61B 2017/0446* (2013.01); *A61B 2017/0453* (2013.01); *A61B 2017/0619* (2013.01); *A61B 2017/8655* (2013.01); *A61B 2090/034* (2016.02); *A61F 2002/285* (2013.01); *A61F 2002/2892* (2013.01); *A61F 2002/30065* (2013.01); *A61F 2002/3092* (2013.01); *A61F 2002/30405* (2013.01); *A61F 2002/30448* (2013.01); *A61F 2002/30807* (2013.01);
(Continued)

(58) Field of Classification Search
CPC ............... A61F 2/2846; A61B 17/0401; A61B 17/06166; A61B 2017/06185; A61B 2017/0619
See application file for complete search history.

(56) References Cited

U.S. PATENT DOCUMENTS 5,372,665 A    12/1994   Chatin et al.
5,434,361 A    7/1995    Chatin et al.
(Continued)

*Primary Examiner* — Si Ming Ku
(74) *Attorney, Agent, or Firm* — Lerner, David, Littenberg, Krumholz & Mentlik, LLP

(57) ABSTRACT

Disclosed herein are an implant with an attachment feature and a method for attaching to the same. The implant may include a cavity with a porous layer disposed within a non-porous layer wherein the non-porous layer defines a chamber. The chamber may receive and confine liquefiable material and direct liquefiable material to permeate through the porous layer. A method of attaching a device to the implant may include liquefying a liquefiable portion of the device and allowing the liquefied material to interdigitate with the second layer and then solidify to prevent pullout.

15 Claims, 11 Drawing Sheets

(51) Int. Cl.
*A61B 17/06* (2006.01)
*A61B 17/86* (2006.01)
*A61F 2/38* (2006.01)
*A61B 17/68* (2006.01)
*A61F 2/40* (2006.01)
*A61F 2/36* (2006.01)
*A61L 27/56* (2006.01)
*A61F 2/30* (2006.01)
*A61B 17/00* (2006.01)
*A61B 17/84* (2006.01)
*A61F 2/46* (2006.01)
*A61B 90/00* (2016.01)

(52) U.S. Cl.
CPC ............... *A61F 2002/4062* (2013.01); *A61F 2002/4683* (2013.01); *A61L 27/56* (2013.01)

(56) References Cited

U.S. PATENT DOCUMENTS

| | | |
|---|---|---|
| 5,665,110 A | 9/1997 | Chervitz et al. |
| 5,993,477 A | 11/1999 | Vaitekunas et al. |
| 6,620,185 B1 | 9/2003 | Harvie et al. |
| 6,626,945 B2 | 9/2003 | Simon et al. |
| 6,632,246 B1 | 10/2003 | Simon et al. |
| 6,703,129 B1 | 3/2004 | Kakehi et al. |
| 6,852,125 B2 | 2/2005 | Simon et al. |
| 6,913,666 B1 | 7/2005 | Aeschlimann et al. |
| 6,921,264 B2 | 7/2005 | Mayer et al. |
| 6,936,270 B2 | 8/2005 | Watson et al. |
| 7,144,414 B2 | 12/2006 | Harvie et al. |
| 7,160,405 B2 | 1/2007 | Aeschlimann et al. |
| 7,335,205 B2 | 2/2008 | Aeschlimann et al. |
| 7,815,409 B2 | 10/2010 | Aeschlimann et al. |
| 7,967,820 B2 | 6/2011 | Bonutti et al. |
| 8,114,137 B2 | 2/2012 | Aeschlimann et al. |
| 8,221,475 B2 | 7/2012 | Aeschlimann et al. |
| 8,221,477 B2 | 7/2012 | Aeschlimann et al. |
| 8,323,323 B2 | 12/2012 | Aeschlimann et al. |
| 8,357,201 B2 | 1/2013 | Mayer et al. |
| 8,403,938 B2 | 3/2013 | Aeschlimann et al. |
| 8,496,657 B2 | 7/2013 | Bonutti et al. |
| 8,545,536 B2 | 10/2013 | Mayer et al. |
| 8,608,743 B2 | 12/2013 | Baumgartner et al. |
| 8,623,050 B2 | 1/2014 | Lehmann et al. |
| 8,663,297 B2 | 3/2014 | Mayer et al. |
| 8,747,439 B2 | 6/2014 | Bonutti et al. |
| D710,997 S | 8/2014 | Thon et al. |
| 8,801,722 B2 | 8/2014 | Aeschlimann et al. |
| 8,834,542 B2 | 9/2014 | Mayer et al. |
| 8,870,572 B2 | 10/2014 | Mayer et al. |
| 8,870,933 B2 | 10/2014 | Aeschlimann et al. |
| 8,906,029 B2 | 12/2014 | Mock et al. |
| 8,911,234 B2 | 12/2014 | Mayer et al. |
| 8,932,337 B2 | 1/2015 | Aeschlimann et al. |
| 8,945,192 B2 | 2/2015 | Aeschlimann et al. |
| 8,950,159 B2 | 2/2015 | Cove et al. |
| 8,955,289 B2 | 2/2015 | Clinch et al. |
| 9,005,184 B2 | 4/2015 | Mayer et al. |
| 9,032,693 B2 | 5/2015 | Clinch et al. |
| 9,089,323 B2 | 7/2015 | Bonutti et al. |
| 9,173,650 B2 | 11/2015 | Bonutti et al. |
| 9,216,083 B2 | 12/2015 | Aeschlimann et al. |
| 9,226,784 B2 | 1/2016 | Lehmann et al. |
| 9,254,585 B2 | 2/2016 | Schmitz |
| 9,289,301 B2 | 3/2016 | Mayer et al. |
| 9,421,005 B2 | 8/2016 | Bonutti et al. |
| 9,445,888 B2 | 9/2016 | Aeschlimann et al. |
| 9,510,861 B2 | 12/2016 | Mayer et al. |
| 9,526,490 B2 | 12/2016 | Mayer et al. |
| 2004/0049194 A1 | 3/2004 | Harvie et al. |
| 2004/0162622 A1 | 8/2004 | Simon et al. |
| 2004/0191106 A1 | 9/2004 | O'Neill et al. |
| 2005/0031665 A1 | 2/2005 | Watson et al. |
| 2005/0079696 A1 | 4/2005 | Colombo |
| 2006/0147332 A1 | 7/2006 | Jones et al. |
| 2007/0142914 A1 | 6/2007 | Jones et al. |
| 2010/0023057 A1* | 1/2010 | Aeschlimann ..... A61B 17/7233 606/246 |
| 2012/0078300 A1 | 3/2012 | Mayer et al. |
| 2012/0156069 A1 | 6/2012 | Yang |
| 2013/0006278 A1 | 1/2013 | Mayer et al. |
| 2013/0268085 A1 | 10/2013 | Dong et al. |
| 2013/0302086 A1 | 11/2013 | Lehmann et al. |
| 2014/0327187 A1 | 11/2014 | Hurdle |
| 2014/0336663 A1 | 11/2014 | Mayer et al. |
| 2014/0364908 A1 | 12/2014 | Mayer et al. |
| 2015/0012091 A1 | 1/2015 | Mayer et al. |
| 2015/0174818 A1 | 6/2015 | Mayer et al. |
| 2015/0182210 A1 | 7/2015 | Mayer et al. |
| 2015/0196253 A1 | 7/2015 | Mayer et al. |
| 2015/0282804 A1 | 10/2015 | Bonutti et al. |
| 2015/0336329 A1 | 11/2015 | Lehmann et al. |
| 2016/0058579 A1 | 3/2016 | Aeschlimann et al. |
| 2016/0074083 A1 | 3/2016 | Aeschlimann et al. |
| 2016/0074085 A1 | 3/2016 | Lehmann et al. |
| 2016/0135961 A1 | 5/2016 | Aeschlimann et al. |
| 2016/0302926 A1 | 10/2016 | Baumgartner et al. |
| 2016/0317141 A1 | 11/2016 | Mayer et al. |
| 2016/0367302 A1 | 12/2016 | Aeschlimann et al. |

\* cited by examiner

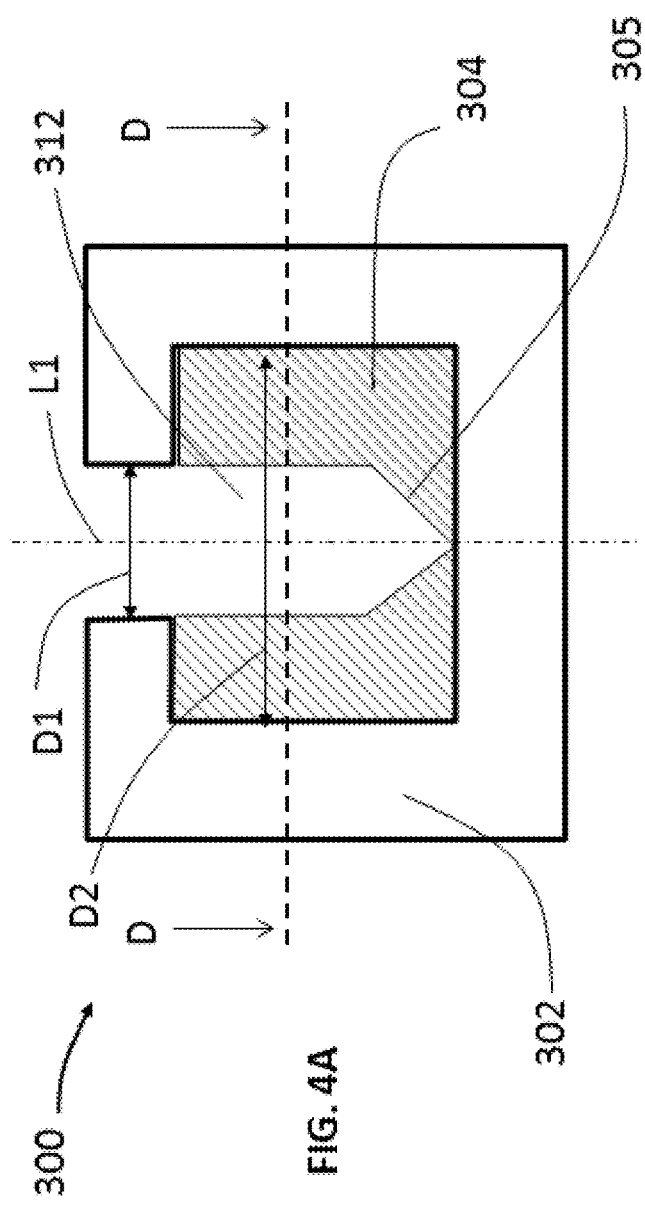
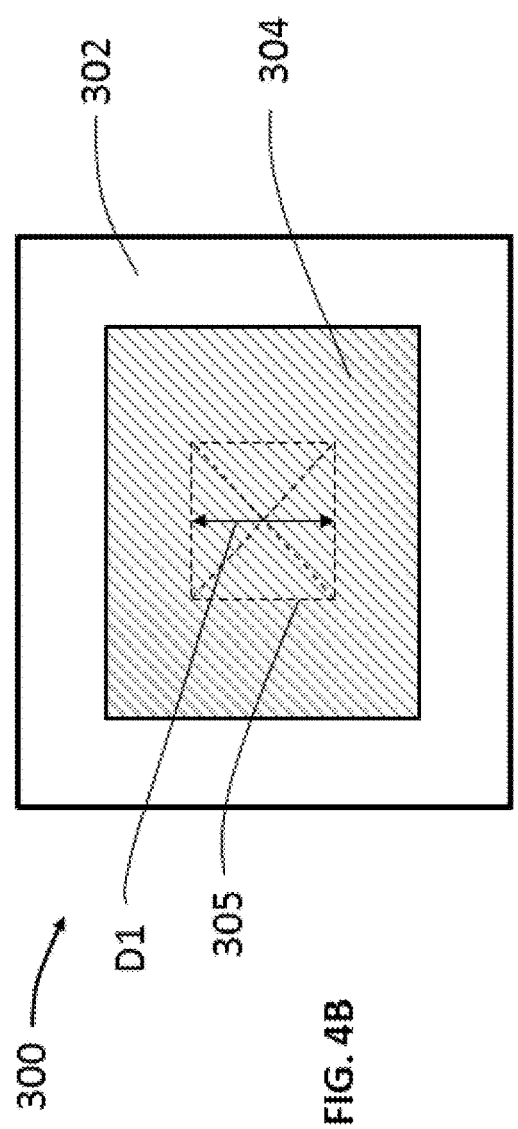
FIG. 4A
FIG. 4B

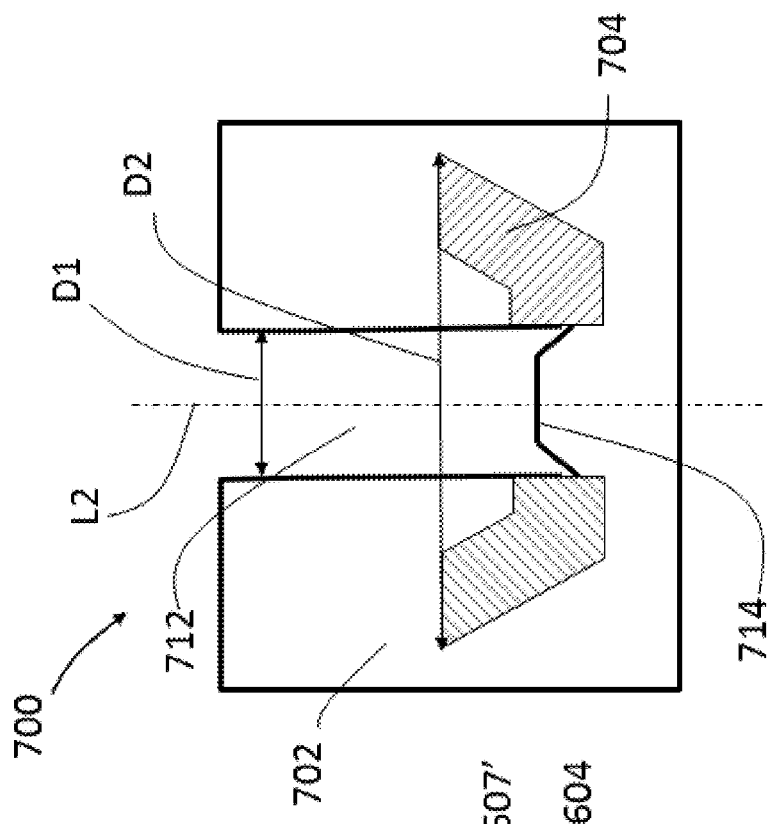
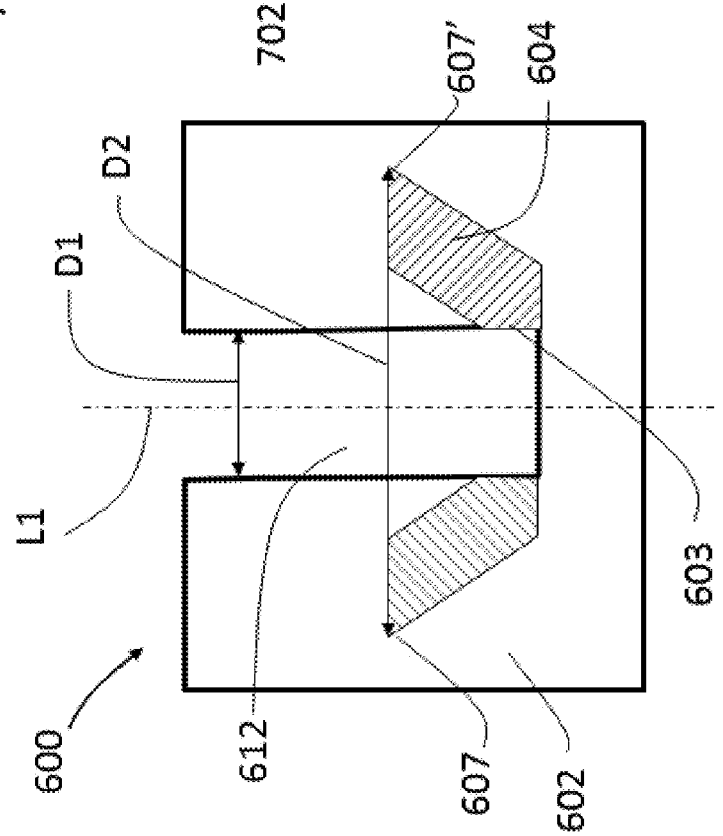

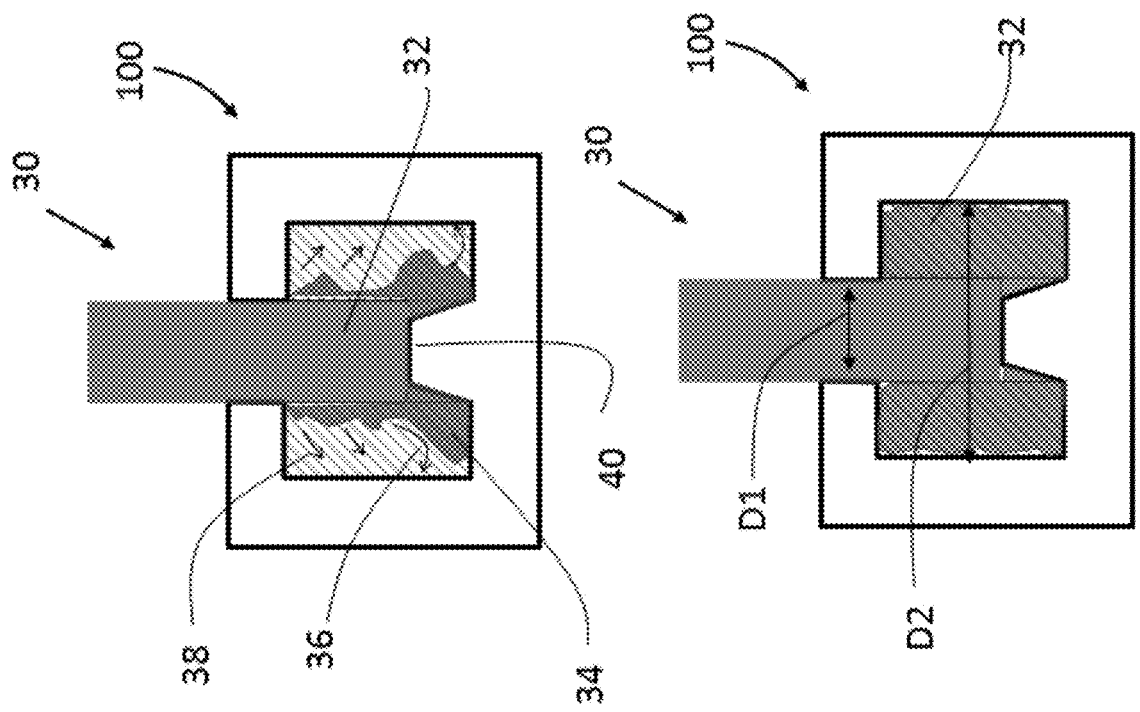
FIG. 10B
FIG. 10C
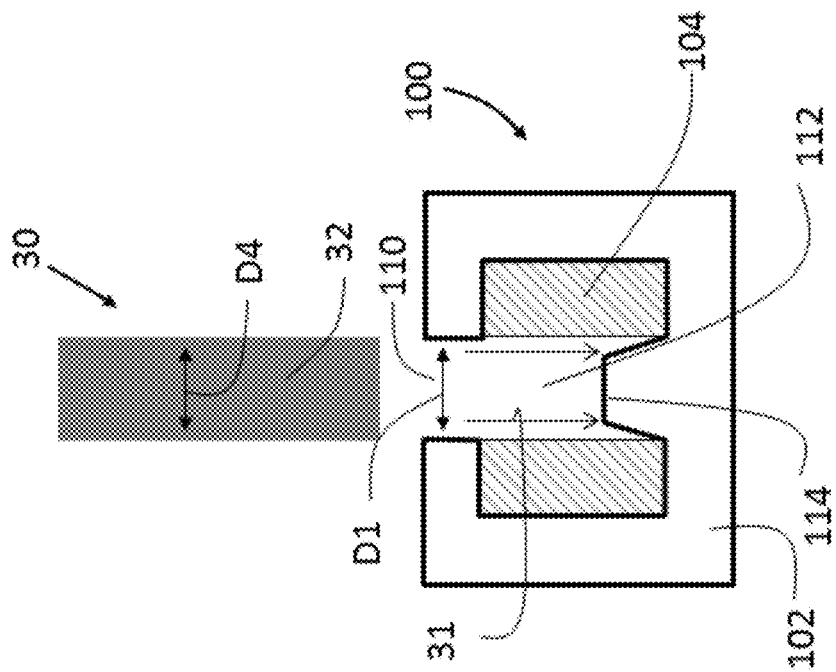
FIG. 10A

IMPLANT WITH HOLE HAVING POROUS STRUCTURE FOR SOFT TISSUE FIXATION

CROSS-REFERENCE TO RELATED APPLICATION

The present application claims the benefit of the filing date of U.S. Provisional Patent Application No. 62/514,318, filed on Jun. 2, 2017, the disclosure of which is hereby incorporated by reference.

FIELD OF INVENTION

The present invention relates generally to an implant with an attachment feature and a method of attaching to the same, and in particular relates to an implant with a cavity having a porous structure and a method for attaching to the same.

BACKGROUND OF THE INVENTION

Surgical implants are generally used in repair or reconstruction of bone fractures, defects, tumors, or other maladies. These surgical procedures may involve the attachment or reattachment of soft tissue to locations in the body, such as to the surgical implant itself. For example, surgical procedures in the proximal tibia, proximal femur, and shoulder may involve repositioning soft tissue and even attaching it to the implant for a successful reconstruction procedure.

Soft tissues are typically attached to implants by sutures, often through suture openings located on the implant. By way of example but not limitation, a fracture occurring in the proximal region of the humerus may require a shoulder stem prosthesis cemented into the humeral medullary canal. The prosthesis may include multiple suture holes by which soft tissues, such as various tendons of the rotator cuff, can be secured to the prosthesis. Attaching sutures to an implant may require considerable time, skill and effort, as it may involve successfully threading the suture through these suture holes and then securing the suture to the implant (e.g., by tying a knot in the suture). Manipulation of sutures through the narrow suture holes, which are often located in tight, inaccessible locations, can be challenging, especially during surgery.

Therefore, there exists a need for an improved implant with attachment features and a method of attaching to the same.

BRIEF SUMMARY OF THE INVENTION

Disclosed herein are implants with attachment features and methods for attaching to the same.

In a first aspect of the present invention, an implant with one or more cavities is provided. Each cavity may include a first non-porous layer defining a chamber with an opening, and a second porous layer within the chamber. The chamber may be configured to receive and confine liquefiable material within the chamber and to allow this material to permeate the second layer.

In accordance with the first aspect, the first layer may be shaped to facilitate permeation of the liquefied material into the second layer by having a feature projecting into the chamber to direct the liquefied material into the second layer. The feature may include a recess having a second portion of the second layer. The feature may also include at least one angled side surface to direct liquefied material to the second layer.

The implant may include an open passageway extending along an axis from the opening to an opposing wall at a distal end of the first surface. The passageway may be surrounded by the second layer and may define a conical shape. The chamber may also be shaped according to any of a cylinder, cuboid, cube, cone, and pyramid. In some aspects, the second layer may be in communication with the open passageway at the distal end and may extend proximally away from the axis.

The implant may further include a device wherein at least a portion of the device may contain liquefiable material. The device may be any of a suture anchor, bone anchor and a second implant. A distal end of the device may have substantially the same dimension as the open passageway and may include an open recess at its distal end. The open recess may have two arms extending distally. Each arm may include a first and a second surface converging at a distal end and define a first angle. The first layer may include a feature projecting into the chamber. The feature may be at least partially surrounded by a portion of the second layer. The feature may include at least one angled side surface directed towards the portion of the second layer defining a second angle. The second angle may be greater than the first angle to allow the feature to direct the liquefied material into the second layer.

The liquefiable material may be substantially solid in a first state and substantially liquid in a second state. The transition from the first state to the second state may be caused by the application of any of heat and ultrasonic energy. The liquefiable material may permeate the second layer in the second state and subsequently transition to the first state upon the removal of any of the heat and ultrasonic energy.

In other aspects, at least one dimension of the chamber may be substantially greater than the opening and may provide additional resistance to device detachment from the implant. The second layer may be a monolithic structure or may include two or more segments. The cavity may be secured to the implant or may be integral with the implant such that the chamber is inseparable from the implant.

In a second aspect of the present invention, an implant having a non-porous first portion is provided. The first portion may define a cavity with an opening containing a porous layer. The cavity may include a second porous layer within the cavity. The cavity may be configured to receive and confine liquefiable material within the cavity and allow that material to permeate the second layer.

A third aspect of the present invention is a method of attaching a liquefiable material to an implant. A method in accordance with this aspect of the invention may include the steps of positioning the liquefiable material in a chamber through an opening of the chamber, the chamber being disposed in a cavity of the implant and defined by a first non-porous layer with a second porous layer disposed within the chamber, and securing the liquefiable material to the implant by allowing the liquefiable material to interdigitate with the second layer in a liquid state and then solidify to prevent pullout of the liquefiable material from the implant. The liquefiable material may be contained in at least a portion of a device.

The method may further include the step of positioning the liquefiable material by placing a distal end of the device in the chamber through the opening, the liquefiable material being in a solid state and applying any of heat energy and ultrasonic energy to transition the liquefiable material from a solid to a liquid state. At least a portion of the first layer may be shaped to direct the permeation of the liquefied material into the second layer.

A fourth aspect of the present invention is a method of fabricating an implant including the steps forming the implant by an additive manufacturing process, the implant having a cavity having a first non-porous layer defining a chamber with an opening and a second porous layer disposed within the chamber.

The method of additive manufacturing the second layer may include the steps of depositing a first band of a metal powder onto the first layer, scanning a beam so as to melt the metal powder at predetermined locations to form a portion of a plurality of porous geometries in the form of predetermined unit cells within the metal powder layer, the porous geometries having a plurality of struts with a length and a cross-section, depositing at least one additional layer of metal powder onto the first band, and repeating the step of scanning a beam for at least some of the additional deposited metal powder layers in order to continue forming the porous geometries of the second layer.

A fifth aspect of the present invention is a method of fabricating an implant including the steps of forming an implant with a cavity, forming an insert comprising a first non-porous layer defining a chamber having an opening and a second porous layer disposed within the chamber, attaching and securing the insert to the cavity.

In a sixth aspect of the present invention, an implant with one or more cavities is provided. Each cavity may include a non-porous layer defining a chamber with an opening. One or more grooves may be disposed around the chamber. The grooves may define a first dimension and a second larger dimension. The chamber may be configured to receive and confine liquefiable material within the chamber to allow this material to collect within the grooves.

In accordance with this sixth aspect, the grooves may be shaped to form internal threading. A minor diameter of the internal threading may be equal to the first dimension and a major diameter may be equal to the second dimension.

A seventh aspect of the present invention is a method of attaching a liquefiable material to an implant. A method in accordance with this aspect may include the steps of positioning the liquefiable material in a chamber through an opening of the chamber, the chamber may be disposed in a cavity of the implant and defined by a non-porous layer, one or more grooves may be disposed around the chamber, each groove may define a first dimension and a second larger dimension, and securing the liquefiable material to the implant by allowing the liquefiable material to collect within the grooves in a liquid state and then solidify to prevent pullout of the liquefiable material from the material. The liquefiable material may be contained in at least a portion of a device.

In accordance with this seventh aspect, the grooves may be configured to form internal threading. A minor diameter of the internal threading may be the same as the first dimension and a major diameter may be equal to the second dimension. The liquefiable may solidify within the chamber and may be imparted with an external threading corresponding to the internal threading.

The method may further include the step of removing the liquefiable material after it solidifies from the chamber by unscrewing the liquefiable material to threadingly disengage from the internal threading.

In an eight aspect of the present invention, an implant with one or more cavities is provided. Each cavity may include a first non-porous layer defining a chamber with an opening, and a second porous layer within the chamber. The chamber may be configured to receive and confine soft tissue within the chamber and to allow soft tissue to permeate the second layer.

BRIEF DESCRIPTION OF THE DRAWINGS

A more complete appreciation of the subject matter of the present invention and the various advantages thereof may be realized by reference to the following detailed description, in which reference is made to the following accompanying drawings:

FIG. 4A is a side cross-sectional view of a cavity according to another embodiment of the present invention;

FIG. 4B is a top cross-sectional view of the cavity of FIG. 4A along line D-D;

FIG. 7 is a side cross-sectional view of a cavity according to yet another embodiment of the present invention;

FIG. 8 is a side cross-sectional view of a cavity according to yet another embodiment of the present invention;

FIGS. 10A-10C are schematic side cross-sectional views of the implant of FIG. 1 showing the sequential steps of attaching a device to the cavity;

DETAILED DESCRIPTION

Figure 1:
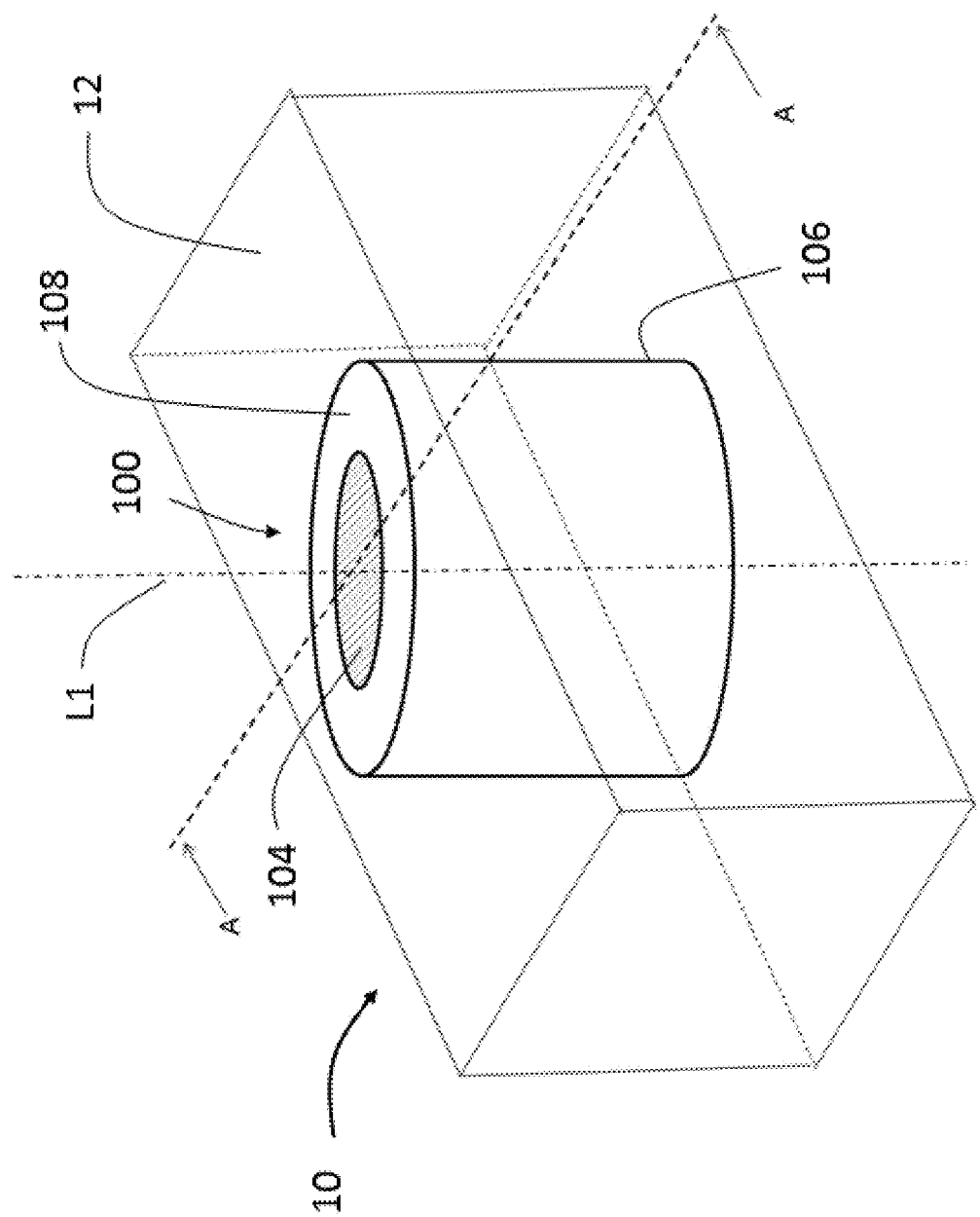
FIG. 1 is a perspective view of a cavity in an implant in accordance with an embodiment of the present invention.

Referring now to FIG. 1, there is shown an implant 10 having a cavity 100 according to an embodiment of the present invention. Implant 10 shown here is only illustrative of various implants that may be provided with cavity 10. A top surface 108 of cavity 100 lies on the same plane as a top surface 12 of implant 10. Outer surface 106 of cavity 100 may be attached to the implant or it may be an integral part of implant 10. For example, cavity 100 may be fabricated to be monolithic with the implant 10, i.e., by an additive manufacturing process, or cavity 100 may be fabricated separately and then secured to implant 10.

Figure 2C:
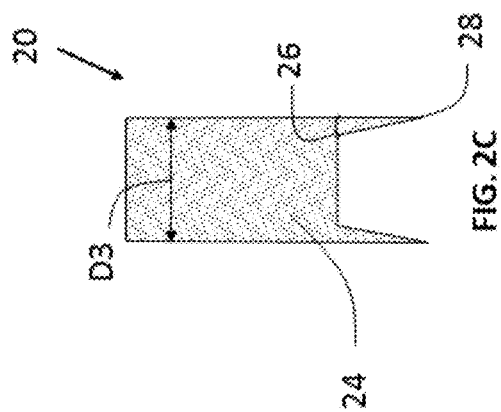
FIG. 2C is a simplified, side cross-sectional view of a distal end of a suture anchor.
Figure 2A:
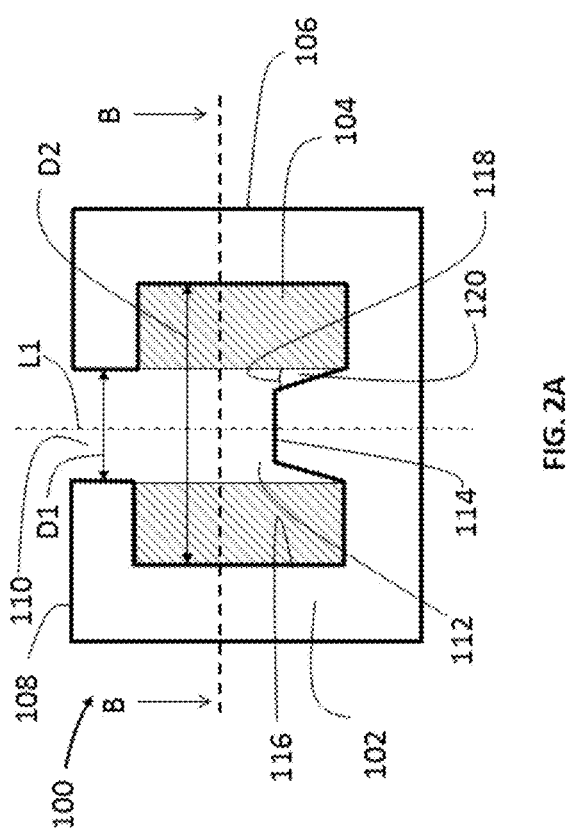
FIG. 2A is a side cross-sectional view of the cavity of FIG. 1 along line A-A.
Figure 2B:
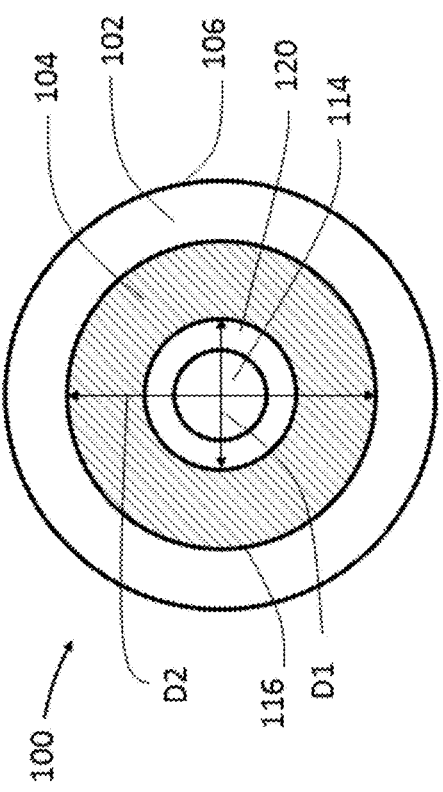
FIG. 2B is a top cross-sectional view of the cavity of FIG. 2A along line B-B.

FIGS. 2A and 2B are side and top cross-sectional views of cavity 100 respectively. Cavity 100 includes a non-porous layer 102 having an outer surface 106 and inner surface 116 forming a chamber. In embodiments where the outer surface 106 of the cavity is formed as an integral part of the implant 10, there may be no defined outer surface 106 of the cavity 100, as it may be continuous with the surrounding material of the implant. An opening 110 at a top surface of the cavity 100 provides access to the chamber. As best seen in FIG. 1, cavity 100 is generally cylindrical in shape with the corresponding chamber defined by inner surface 116 also being generally cylindrical in shape. An inner porous layer 104 is disposed within the chamber and around a longitudinal axis L1 extending through opening 110. Porous layer 104 forms an open passageway 112 extending from opening 110 to an elevated platform 114 located at an opposite end of inner surface 116. A first length D1 measured at opening 110 is less than a second length D2 defined by the chamber. As used herein the term "chamber" refers to the space enclosed by inner surface 116, i.e., the passageway 112 and the porous layer 104. In this embodiment, the distance between inner surfaces of porous layer 104 defining passageway 112 is the same as first length D1. Consequently, the passageway 112 serves as a channel to guide an attachment device from opening 110 to platform 114.

A suture (e.g. for attaching soft tissue to the implant 10) may be secured to the cavity 100. For example, the suture (not shown) may be secured to the cavity 100 by a flowable material that is caused to flow within the chamber and then solidify, thus anchoring the suture within the cavity 100. The suture itself may be positioned within the chamber, such that it becomes embedded in the flowable material when it solidifies. An example of such a flowable material may be a curable cement or a melted thermoplastic material. Such material(s) may be poured into the cavity 100 in a flowable state, either before or after the suture is positioned within the cavity 100. While it is in a flowable state, the flowable material may spread out within the chamber (which has a larger diameter D2 than the opening 110, as discussed above), thus anchoring the suture in the cavity 100 by solidifying in a configuration which cannot be pulled through the smaller opening 100. Alternatively or additionally, while in the flowable state, the flowable material may interdigitate with the porous layer 104, so as to anchor the suture in the cavity 100 when the material solidifies.

In other alternative embodiments, the flowable material may be positioned in the cavity 100 in a solid state and then caused to transition to a flowable state before re-solidifying. As an example, a solid thermoplastic component shaped to fit within the passageway 112 may be positioned therein, after which at least a portion of that component can be melted so as to become flowable. Such melting might be induced by a heating element (e.g., a resistive heating element) in contact with the thermoplastic component, or the thermoplastic component may be remotely heated by directing electromagnetic radiation (e.g., microwaves or infrared waves) at it. That remotely applied electromagnetic radiation may be in the form of coherent waves (e.g., masers or lasers).

In another example, the solid thermoplastic component may be melted within the cavity 100 by application of ultrasonic vibratory energy, such as by using the technique discussed below or those disclosed in U.S. Pat. Nos. 7,335,205 and 8,403,938, the entire disclosures of which are incorporated herein by reference. Suitable thermoplastic materials for forming such solid component to be melted with ultrasonic vibratory energy are disclosed in those patents. The meltable component may be formed entirely or partially out of the thermoplastic material and shaped into a solid suture anchor. The suture anchor may also have one or more passages, channels, and/or apertures for receiving a suture therethrough so as to secure the suture to the suture anchor. An example of a suitable suture anchor design is illustrated in U.S. Design Pat. No. D710,997, the entire disclosure of which is incorporated herein by reference.

In another example, soft tissue material can be introduced directly into passageway 112 and allowed to grow into porous layer 104 fixating an implant directly to soft tissue. Non-porous layer 102 may be configured to direct and contain soft tissue growth within the chamber to maximize fixation. Implants may be provided with a first set of cavities to receive liquefiable material into porous layers and a second set of cavities to allow soft tissue growth directly into porous layers. The first set of cavities may facilitate initial fixation and the second set of cavities gradually increase and retain fixation by allowing soft tissue growth into porous layers.

FIG. 2C is a simplified, side cross-sectional view of a distal end of a suture anchor 200. Suture anchor 20 shown here is only an example of an attachment device that may be secured to cavity 100, and not meant to be limiting in any way. Suture anchor 20 has a thickness measured by a dimension D3, which is substantially the same as D1. Therefore, suture anchor 20 may be guided through opening 110 and along passageway 112 to contact platform 114. Elevated sides of platform 114 form an angle 118 with an inner side of porous layer 104 and define a pocket 120 as best seen in FIG. 2A. A corresponding angle 26 formed at the distal end of suture anchor 20 is smaller than angle 118. This allows distal tip 28 of suture anchor 20 to contact a distal tip of pocket 120 when placed in passageway 112.

The suture anchor 20 is liquefied within the cavity 100 by contacting the proximal end of the suture anchor 20 with an ultrasonic sonotrode and using the sonotrode to press the suture anchor 20 distally towards the platform 114 while applying ultrasonic vibratory energy to the suture anchor 20. That vibratory energy preferably creates internal friction within the suture anchor 20 and/or between the suture anchor 20 and the contacting surfaces of the implant 10, such as the surfaces of the porous layer 104 alongside the passageway 112 and/or the distal contact surface (e.g., on platform 114). The ultrasonic melting can be controlled in part by selecting an appropriate relationship between dimensions D1 and D3. For example, creating a relatively tight fit within the passageway may increase friction (and corresponding melting) along the outer surface of the suture anchor 20. The liquefied material may also be directed outwardly, e.g., by the angled surfaces of platform 114, so as to distribute and permeate/interdigitate into porous layer 104. Furthermore, the inner surface 116 of non-porous layer 102 desirably confines the liquefied material within the chamber. Consequently, varying the shape of the chamber may allow for controlling the liquefied material permeation. Once the energy application is removed, the interdigitated thermoplastic material cools and transitions back from liquid to solid state, thereby anchoring suture anchor 20 to cavity 100 and preventing pullout. The solidified material will preferably span a substantial or the entire width of chamber, i.e., corresponding to D2, which, due to the narrower opening 110 defined by D1, further aids in anchoring suture anchor 20 and prevents pullout.

Figure 3A:
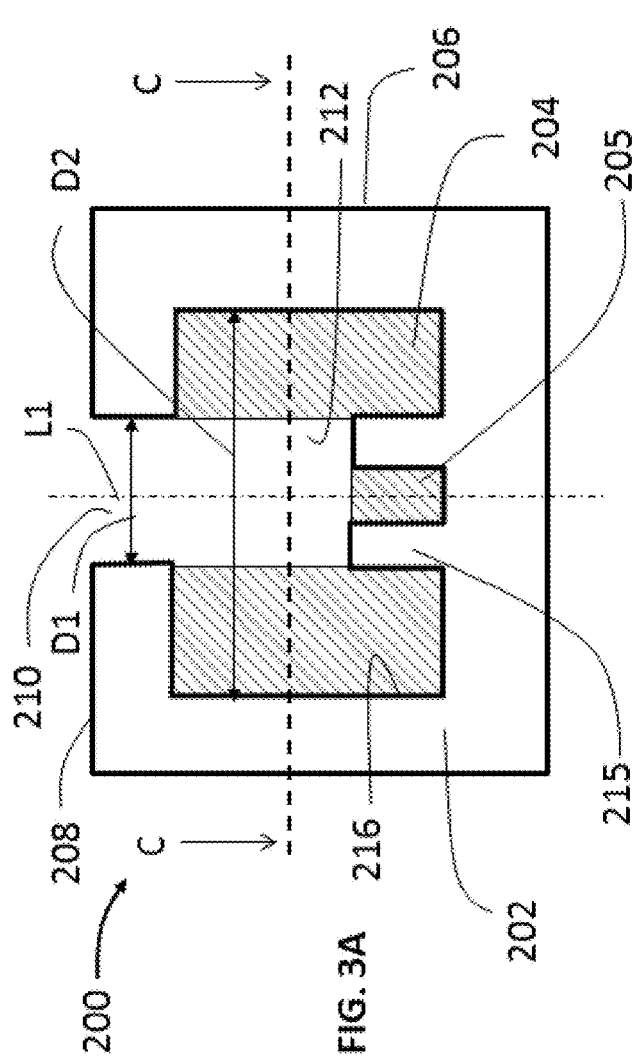
FIG. 3A is side cross-sectional view of a cavity according to another embodiment of the present invention.
Figure 3B:
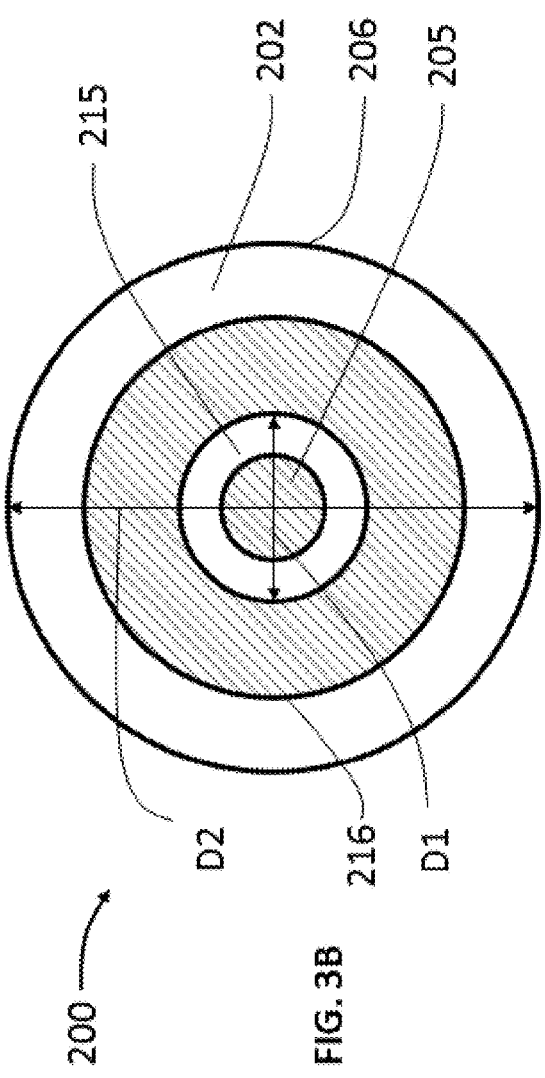
FIG. 3B is a top cross-sectional view of the cavity of FIG. 3A along line C-C.

FIGS. 3A and 3B are side and top cross-sectional views of cavity 200 respectively according to another embodiment. Cavity 200 is similar to cavity 100, and therefore like elements are referred to with similar reference numerals within the 200-series. For instance, cavity 200 also includes a non-porous layer 202 enclosing a chamber with an inner porous layer 204. However, porous layer 204 includes two segments in this embodiment with a porous segment 205 centered around longitudinal axis L1. As best seen in FIG. 3B, porous segment 205 is completely surrounded by a band 215 of non-porous layer 202. Liquefiable material received in passageway 212 will permeate porous layer 204 similar to the permeation of porous layer 104 in cavity 100 described above, but will also include permeation of the porous segment 205 in this embodiment. An attachment device attached to cavity 200 will be attached to porous segment 205 and aligned along axis L1. Consequently, any pullout force experienced by the attached device will include a normal force component acting on porous segment 205, and thereby provide additional resistance to device detachment from implant 10.

Referring now to FIGS. 4A and 4B, there is shown side and top cross-sectional views respectively of cavity 300 according to another embodiment. Cavity 300 is similar to cavity 100, and therefore like elements are referred to with similar reference numerals within the 300-series. Cavity 300 is cuboidal in this embodiment with non-porous layer 302 forming a chamber that is also cuboidal. Porous layer 304 is disposed around longitudinal axis L1 to form a square or rectangular shaped passageway 312. All four sides 305 of porous layer 304 converge at the distal end and are configured to match a distal tip of an attachment device (not shown).

Figure 5:
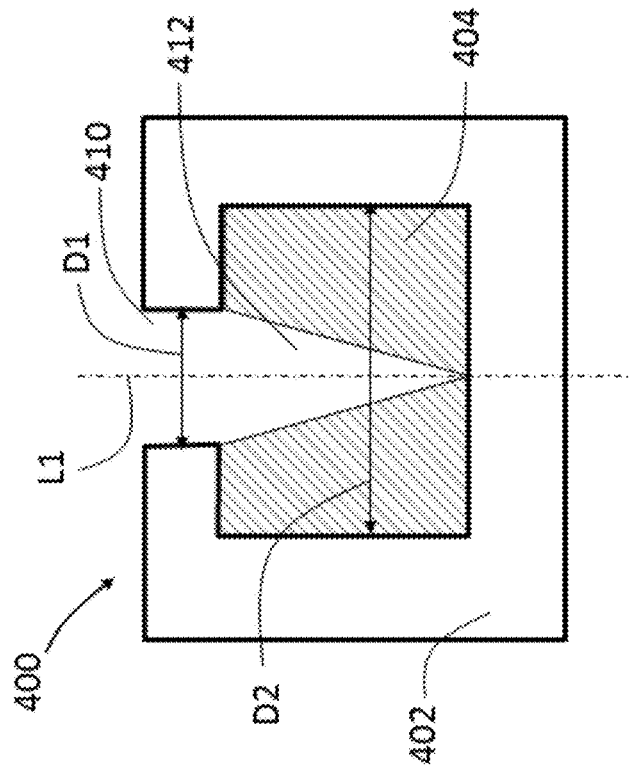
FIG. 5 is a side cross-sectional view of a cavity according to another embodiment of the present invention.

FIGS. 5, 6, 7, and 8 are further illustrations of side cross-sectional views of cavities according to other embodiments of the present invention. Cavities 400, 500, 600 and 700 shown in FIGS. 5, 6, 7, and 8 respectively are similar to cavity 100, and therefore like elements are referred to with similar reference numerals within the corresponding series. Referring now to FIG. 5, cavity 400 may be cylindrical or cuboidal with porous structure 404 arranged around longitudinal axis L1 to form passageway 412. Passageway 412 uniformly tapers from opening 410 to a single point at a distal end of the chamber and may be configured to match a distal end of an attachment device.

Figure 6:
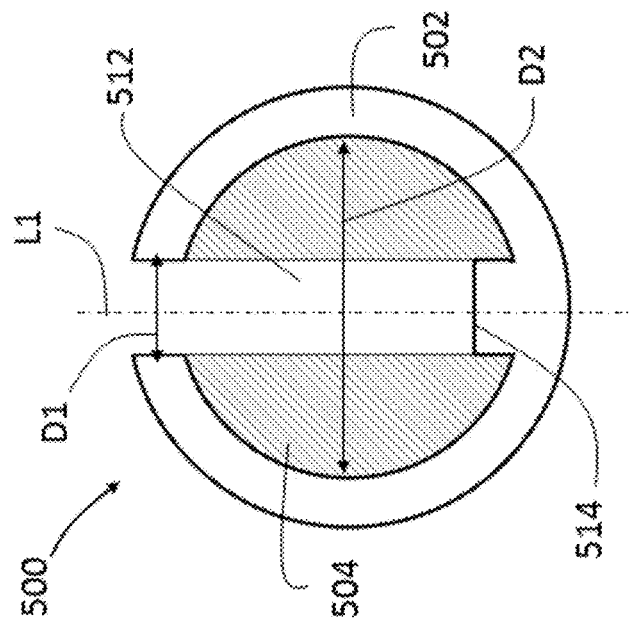
FIG. 6 is a side cross-sectional view of a cavity according to another embodiment of the present invention.

FIG. 6 shows a spherical cavity 500 with non-porous layer 502 defining a spherical chamber. Porous structure 504 is disposed in the chamber around a central axis L1 forming a cylindrical passageway 512. Elevated platform 514 of non-porous layer 502 is located at a distal end of passageway 512 and allows liquefied material to uniformly distribute and permeate porous layer 504.

FIG. 7 shows cavity 600 where the non-porous layer 602 forms a substantial portion of passageway 612. Porous layer 604 is disposed around axis L1 and communicates with passageway 612 at a distal end 603 of the passageway. Porous layer 604 extends proximally from distal end 603 into non-porous layer 600. The maximum width of the chamber is represented by dimension D1. When liquefied material of an attachment device is introduced in passageway 612, the liquefied material will permeate through the porous layer and extend proximally from distal end 603. When this material solidifies, the solidified material may span all of a portion of length D2 from location 607 to location 607' as best shown in FIG. 7. Therefore, the attached device will have an anchoring base (D2) which is substantially greater than passageway 612 (D1), thereby adding to the pullout resistance of the device from the implant. FIG. 8 shows cavity 700 which is substantially similar to cavity 600. Here, the distal end of passageway 700 terminates in elevated platform 714 with sloped surfaces allowing for improved direction of the liquefied material into the porous region 704. As explained in the description of cavity 600, any device attached to cavity 700 may have an anchoring base (D2) which is substantially greater than passageway (D1) to add to the pullout resistance of attached device.

Figure 9:
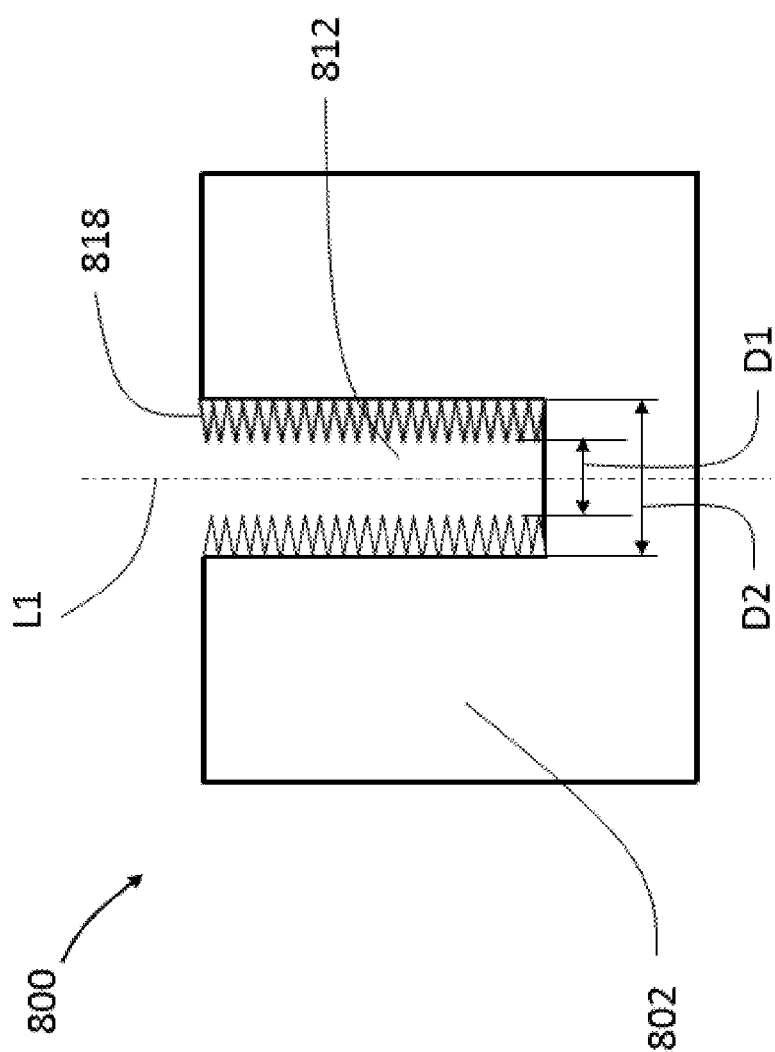
FIG. 9 is side cross-sectional view of a cavity according to yet another embodiment of the present invention.

Referring now to FIG. 9, there is shown a cross-sectional view of a cavity 800 according to another embodiment. Cavity 800 includes an opening 812 disposed within a non-porous layer 802. Non-porous layer 802 includes internal screw threads 818 disposed around the inner walls of opening 812, which allows the opening to function as a screw hole having a minor diameter D1 and a major diameter D2. As more fully explained below, a suture anchor 90 (shown in FIGS. 11A-11C) can be secured to cavity 800 by causing flowable material in suture anchor 90 to flow and solidify in opening 812. Solidified suture anchor 90 will thus be imparted with external threads that match internal screw threads 818 and consequently suture anchor 90 can be threadingly engaged with opening 812. Such threaded engagement desirably secures the suture anchor 90 to cavity 800, thus preventing pullout. Threading engagement of suture 90 with opening 812 will also allow for removal of suture anchor 90 from cavity 800 by rotating and threadingly disengaging suture anchor 90 from cavity 800. Internal screw threads 818 may be configured to control the interaction between the suture anchor and the cavity. For example, increasing the delta between major diameter D2 and minor diameter D1 will maximize pullout resistance, and decreasing the delta between major diameter D2 and minor diameter D1 will allow for easier removal of suture anchor from cavity and minimize time required for solidification. While internal screw threads 818 disposed throughout opening 812 are shown in FIG. 9, other embodiments may have internal threads located only partially around opening 812. Other embodiments may not have internal threads but rather projections formed from the non-porous section that define a first dimension D1 and a larger second dimension D2, whereby the solidified suture anchor assumes the second dimension D2 in at least some portions and therefore cannot be pulled through the smaller opening(s) D1.

While cavities and chambers having cylindrical, cuboidal and spherical shapes are described herein, other cavities may be shaped in any other form such as a cone or a pyramid. Similarly, the passageway may also may be shaped in any other form and configured to optimize flow and permeation of the liquid material. Alternatively, the chamber may be completely filled with a porous layer in other embodiments. The top surface of the cavity may be covered by an overmold made of polyetheretherketone ("PEEK") or other similar material to protect the attached device from tearing or shearing away from rough or sharp edges of the implant. Cavities described herein may be used in any implant, such as but not limited to, hip, knee, shoulder and foot implants. Cavities may be suitably located and distributed across the implants to aid in readily securing attachment devices. Attachment devices may include suture anchors, bone anchors, bone screws, other implants, and other similar devices.

The non-porous layer of the present disclosure may be but is not limited to being made of any polymer such as PEEK, carbon fiber reinforced PEEK, polyaryletherketones ("PAEK"), ultra-high molecular weight polyethylene ("UHMWPE"), metals, or other suitable material (e.g., ceramic) that is biocompatible and possess sufficient strength and rigidity. The porous structure may be but is not limited to being made of any of titanium foam, titanium alloys, stainless steel, cobalt chrome alloys, tantalum and niobium or other suitable material.

Other aspects of the present invention are methods for attaching a device to an implant. Referring now to FIGS. 10A-10C, there is shown a method of attaching a suture anchor 30 to implant 10 having cavity 100. A distal end of suture anchor 30 is positioned in passageway 112 as shown in FIG. 10A. A thickness D4 corresponding to the thickness of suture anchor 30 is substantially the same as passageway 112 dimension D1 defined by porous layer 104 and opening 110 defined by non-porous layer 102. Consequently, passageway 112 serves as a guide to direct suture anchor 30 through passageway 112 from opening 110 to elevated platform 114 as indicated by direction arrows 31. A portion of suture anchor 30 may be made of a suitable thermoplastic material which may change from a solid state 32 to a liquid state 34 upon the application of energy. For example, the suture anchor 30 may have a thermoplastic outer layer surrounding a core of a different material, such as metal. Alternatively, the entire suture anchor may be made of a thermoplastic material. Once suture 30 anchor is at least partially located in passageway 112, ultrasonic energy may be applied to suture anchor 30.

As shown in FIG. 10B, the application of ultrasonic energy (as well as, optionally, distally applied pressure) begins to liquefy thermoplastic material of suture anchor 30 around its periphery, i.e., contact surfaces within cavity 100. Liquefied material 34 at distal tip 40 in contact with elevated platform 114 is forced by the sides of elevated platform into porous section 104 as indicated by directional arrow 36. Further liquefaction of suture anchor 30 takes place along contact surfaces with porous region 104 as indicated by directional arrows 38 showing permeation of liquefied material 34. Application of ultrasonic energy may continue until the entire chamber is filled with liquefied material 34 or achieves a desired level of permeation short of being entirely filled. Once the application of ultrasonic energy is stopped, the liquefied material will cool such that it begins to transition back to a solid state 32. The transition to liquid, permeation, and re-transition back to a solid allows liquefied material 34 to interdigitate with porous layer 102 and form a strong bond. Further, as best seen in FIG. 10C a solidified portion, now part of suture anchor 10, defines a length D2 which is substantially greater than the length of opening 110 (D1). This adds to the securement of suture anchor 10 to cavity 100 and prevents backout of suture anchor 10. While an application of ultrasonic energy has been discussed here, any other form of energy appropriate to cause melting and/or liquefaction of the material in the attachment device may alternatively be used.

Figures 11A, 11B, 11C:
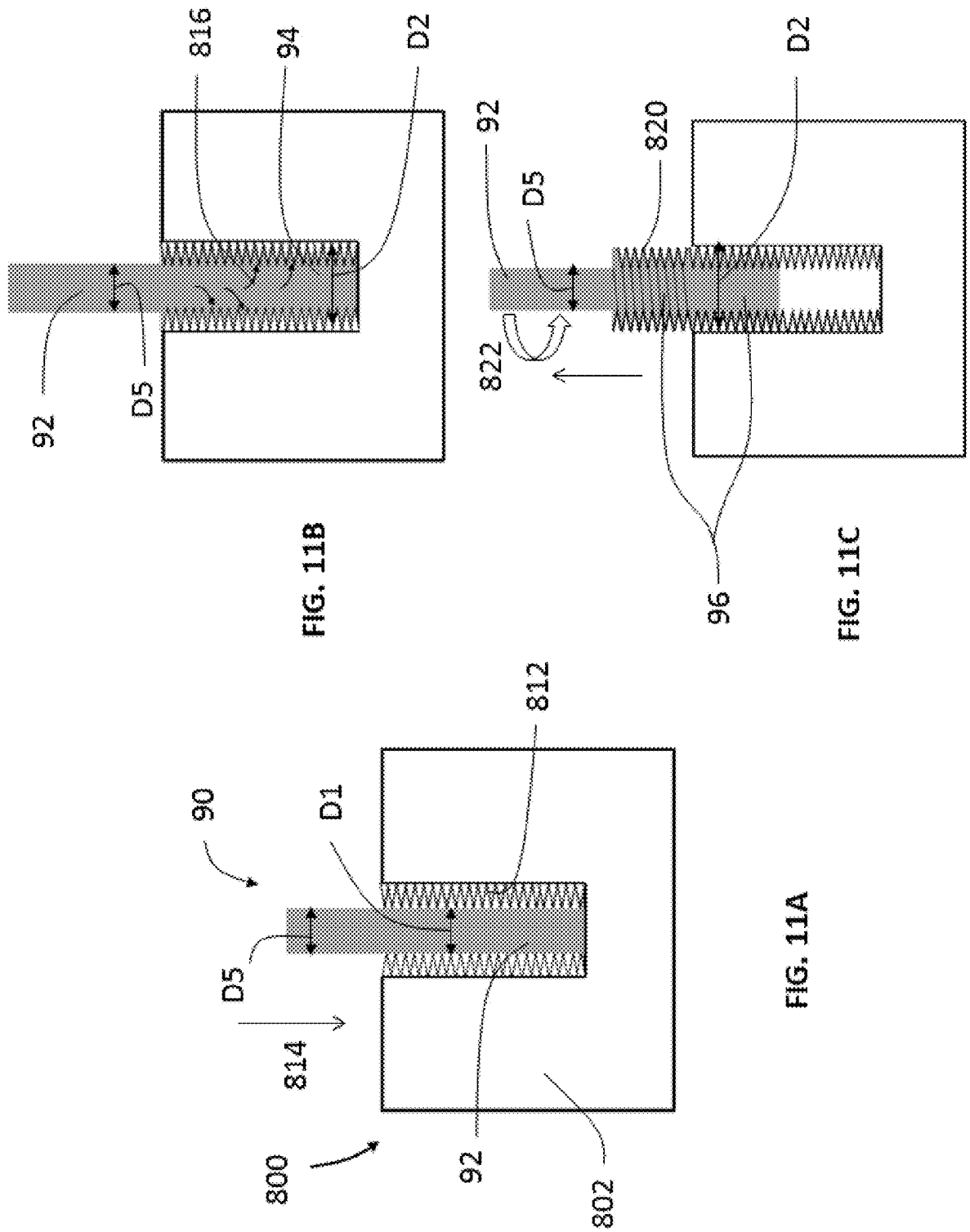
FIGS. 11A-11C are schematic side cross-sectional views of the implant of FIG. 9 showing the sequential steps of attaching and detaching a device to the cavity.

FIGS. 11A-11C show a method of attaching a suture anchor 90 to cavity 800 according to another aspect of the present invention. A distal end of suture anchor 90 is guided into passageway 812 as shown by direction arrow 814 in FIG. 11A. A thickness D5 corresponding to the thickness of suture anchor 90 is substantially the same as minor diameter D1 of internal screw threads 818 thereby establishing contact between the suture anchor 90 and passageway 812. A portion of suture anchor 90 may be made of a suitable thermoplastic material which may change from a solid state 92 to liquid state 94 upon the application of energy. Similar to suture anchor 30, suture anchor 90 may have a thermoplastic outer layer surrounding a core of a different material, such as metal, or may entirely be made of a thermoplastic material. Once suture 90 anchor is at least partially located in passageway 812, ultrasonic energy may be applied to suture anchor 90. Liquefied material 94 flows into the gaps between minor diameter D1 and major diameter D2 as shown by flow arrows 816 in FIG. 11B. Consequently, a distal portion 96 of suture anchor 90 conforms and acquires the shape of internal threads 818. Once the application of ultrasonic energy is stopped, liquefied material 94 will cool and transition back to a solid state. Solidified distal portion 96 will acquire external threads 820 corresponding to internal threads 812 with minor diameter D5, which is the same as D1, and major diameter D2. As best seen in FIG. 11C, suture anchor 90 will now have a proximal portion 92 with dimension D5 and a thicker distal portion 96 with external screw threads 820 ensuring that suture anchor 90 is securely attached to cavity 800. If needed, for example because the suture needs to be removed or the suture anchor needs to be replaced, the threads permit the suture anchor 90 to be threadingly disengaged from cavity 800 by unscrewing the suture anchor from passageway 812 as indicated by directional arrow 822. While an application of ultrasonic energy has been discussed here, any other form of energy appropriate to cause melting and/or liquefaction of the material in the attachment device may alternatively be used.

Figure 13:
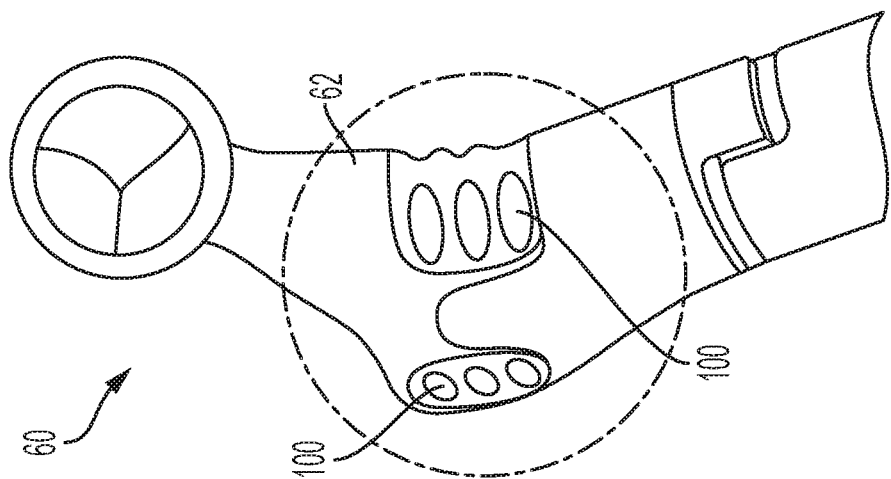
FIG. 13 is a perspective view of a hip implant with a cavity of the present invention.
Figure 12:
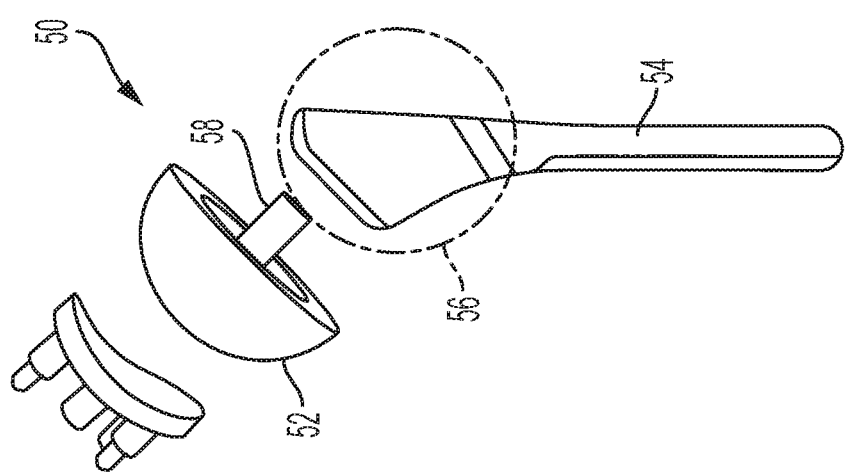
FIG. 12 is a perspective view of a shoulder implant with a cavity of the present invention.
Figure 15:
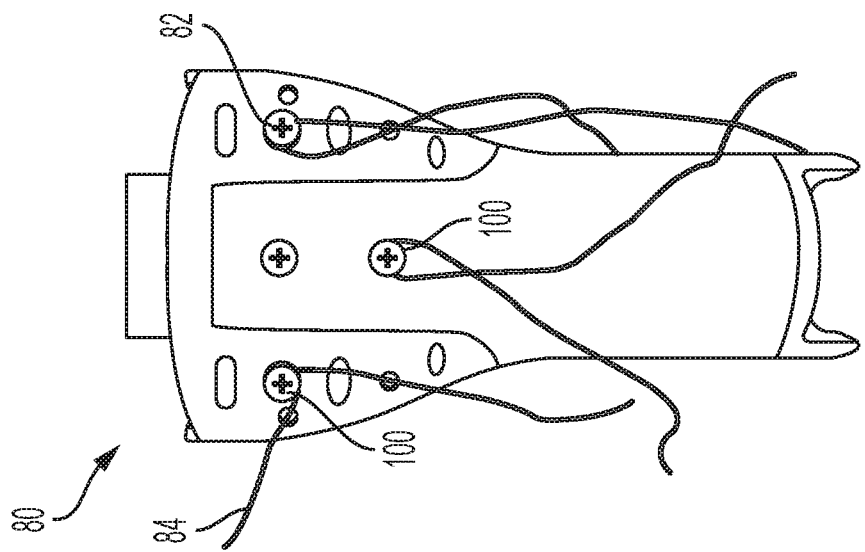
FIG. 15 is a perspective view of a 3-D printed proximal tibial implant with a suture anchor secured to a cavity of the present invention.
Figure 14:
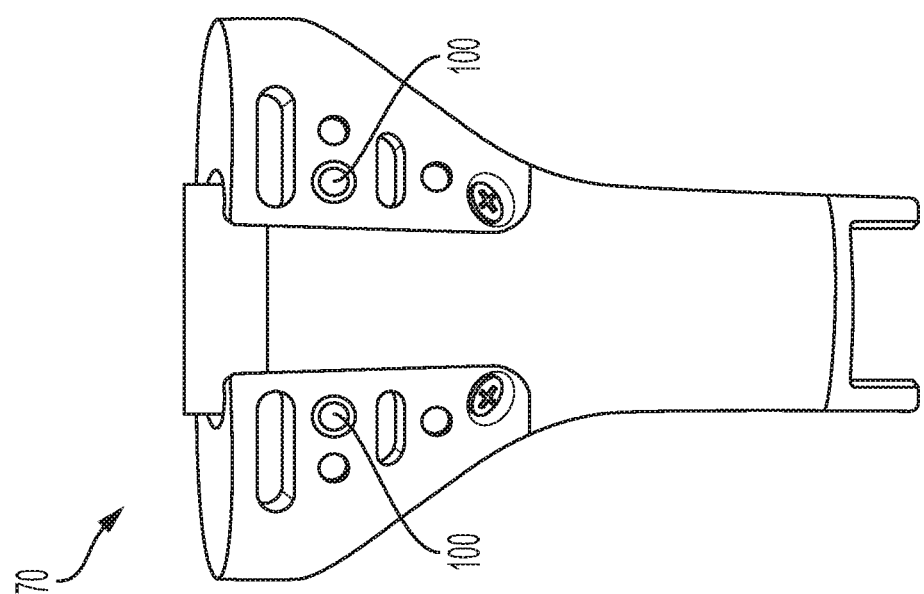
FIG. 14 is a perspective view of a proximal tibial implant with a cavity of the present invention.

FIGS. 12-15 show exemplary implants with locations for cavities serving as attachment features. FIG. 12 depicts a shoulder implant 50 having a humeral stem component 54 that can be attached to a glenoid sphere component 52. A proximal region 56 of implant 50 may include one or more of the cavities disclosed herein (not shown) for attachment of soft tissue. One or more posts 58 on glenoid sphere component 52 could also be attached to one or more appropriately sized cavities (not shown) located on a proximal surface of humeral stem component 54 using the attachment structures and methods disclosed herein. FIG. 13 shows a hip implant 60 with cavities 100 located on two sides of a femoral neck component 62. Cavities 100 of femoral neck component 62 can be used to attach suture anchors as described above. FIG. 14 is a perspective view of a proximal tibial implant 70 with cavities 100 located on two sides. FIG. 15 is a 3-D printed proximal tibial implant 80 with suture anchors 82 attached to cavities 100. Suture anchors 82 can be secured to implant 80 as described above, whereby sutures 84 attached to suture anchors 82 are now firmly secured to implant 80. Exemplary implants described here are merely illustrative of the principles and applications of the present invention and as such the attachment features of the present invention may be used in conjunction with any implant.

A further aspect of the present invention is a step of manufacturing an implant with the cavity described herein. The implant may be fabricated with the cavity being integral to the implant, or the cavity may be fabricated separately and then attached to the implant by snap-fitting, gluing, welding or screwing. Any additive manufacturing process such as three-dimensional (3D) printing or the like may be used to manufacture the implant and the cavity. Porous layers in the cavity may be a titanium or other metallic foam fabricated by utilizing any of the following additive manufacturing processes: (1) beam overlap fabrication disclosed in U.S. Patent Publication No. 2004/0191106, (2) tessellated unit cell fabrication disclosed in U.S. Patent Publication No. 2006/0147332, (3) laser and e-beam polymer interdigitation disclosed in U.S. Patent Publication No. 2007/0142914, (4) conformal surfaces fabrication disclosed in U.S. Patent Publication No. 2013/0268085, or (5) mesh and chain mail fabrication disclosed in U.S. Patent Publication No. 2012/0156069. The disclosures of all of the above applications and publications are hereby incorporated by reference herein. The porous structure may be but is not limited to being made as a single construct that covers substantially the entire chamber (as shown for example in FIG. 2A), or composed of multiple segments (as shown for example in FIG. 3A). Other suitable biocompatible materials as described above may also be used depending on the desired porosity of the porous structure.

Furthermore, although the invention disclosed herein has been described with reference to particular features, it is to be understood that these features are merely illustrative of the principles and applications of the present invention. It is therefore to be understood that numerous modifications, including changes in the sizes of the various features described herein, may be made to the illustrative embodiments and that other arrangements may be devised without departing from the spirit and scope of the present invention. In this regard, the present invention encompasses numerous additional features in addition to those specific features set forth in the paragraphs below. Moreover, the foregoing disclosure should be taken by way of illustration rather than by way of limitation as the present invention is defined in the examples of the numbered paragraphs, which describe features in accordance with various embodiments of the invention, set forth in the claims below.

The invention claimed is:

1. An implant having one or more cavities, each cavity comprising:
    a non-porous first layer defining a chamber having an opening;
    a porous second layer;
    wherein the second layer is disposed within the chamber such that when a liquefiable material is received in the chamber through the opening, the liquefiable material permeates into the second layer and is confined within the chamber by the first layer.

2. The implant of claim 1, wherein at least a portion of the first layer is shaped to direct the permeation of the liquefied material into the second layer.

3. The implant of claim 2, wherein the first layer includes a feature projecting into the chamber, the feature being at least partially surrounded by a portion of the second layer, such that the feature directs the liquefied material into the portion of the second layer.

4. The implant of claim 3, wherein the feature includes at least one angled side surface directed towards the portion of the second layer.

5. The implant of claim 1, wherein the chamber includes an open passageway extending along an axis from the opening towards an opposing wall, the second layer surrounding the open passageway about the axis.

6. The implant of claim 1, further comprising a device wherein the liquefiable material is a portion of the device.

7. The implant of claim 6, wherein the device is any of a suture anchor, bone anchor and a second implant.

8. The implant of claim 7, wherein a distal end of the device has substantially the same dimension as the open passageway.

9. The implant of claim 7, wherein the device is a suture anchor having an open recess defined at its distal end, the recess being defined by two arms extending distally, each arm comprising of a first and a second surface converging at a distal end and defining a first angle, the first layer including a feature projecting into the chamber, the feature being at least partially surrounded by a portion of the second layer, such that the feature directs the liquefied material into the portion of the second layer, the feature including at least one angled side surface directed towards the portion of the second layer defining a second angle, such that the second angle is greater than the first angle.

10. The implant of claim 1, wherein the liquefiable material is substantially a solid in a first state and substantially a liquid in a second state, the liquefiable material permeating into the second layer in the second state and subsequently transitioning to the first state.

11. The implant of claim 10, wherein the liquefiable material transitions from the first state to the second state by the application of any of heat energy and ultrasonic energy, and back to the first state by the removal of any of the heat and ultrasonic energy.

12. The implant of claim 1, wherein at least one dimension of the chamber measured parallel to the opening is substantially the same or greater than the opening.

13. The implant of claim 1, wherein the chamber is shaped according to any of a cylinder, sphere, cuboid, cube, cone and pyramid.

14. The implant of claim 1, wherein the first and second layers are integral to the implant such that the chamber is inseparable from the implant.

15. An implant comprising:
    a non-porous first portion;
    a cavity defined within the first portion, the cavity having an opening;
    a porous layer;
    wherein the porous layer is disposed within the cavity such that when a liquefiable material is received in the cavity through the opening, the liquefiable material permeates into the porous layer and is confined within the chamber by the first portion.

* * * * *